US00PP13137P2

(12) United States Plant Patent
Oliver

(10) Patent No.: US PP13,137 P2
(45) Date of Patent: Oct. 29, 2002

(54) HEUCHERA PLANT NAMED 'JADE GLOSS'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/014,464

(22) Filed: Dec. 8, 2001

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,111 P * 10/1999 Oliver ..... Plt./263
PP12,066 P2 * 8/2001 Oliver ..... Plt./263

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Heuchera plant named 'Jade Gloss', characterized by its full and uniformly mounded plant habit; silvery gray and dark gray green-colored upper leaf surfaces; dark red purple-colored lower leaf surfaces; numerous showy white-colored flowers arranged on erect panicles; and excellent garden performance.

1 Drawing Sheet

BOTANICAL CLASSIFICATION/CULTIVAR DESIGNATION

*Heuchera sp.* cultivar Jade Gloss.

BACKGROUND OF THE INVENTION

The present invention relates to a new and distinct cultivar of Heuchera plant, botanically known as *Heuchera sp.* and hereinafter referred to by the name 'Jade Gloss'.

The new Heuchera is a product of a planned breeding program conducted by the Inventor in Scottdale, Pa. The objective of the breeding program is to create new Heuchera cultivars having good plant vigor, dense and uniform plant habit, and showy and attractive flower and leaf coloration.

The new Heuchera was discovered by the Inventor in a controlled environment in Scottdale, Pa., from seedling progeny from a self-pollination made by the Inventor in May, 1998, of the Heuchera cultivar Silver Maps, not patented. The new Heuchera was selected by the Inventor in May, 1999. The selection of this plant was based on its desirable flower and foliage coloration.

Asexual reproduction of the new Heuchera by cuttings taken in a controlled environment in Scottdale, Pa., since August, 1999, has shown that the unique features of this new Heuchera are stable and reproduced true to type in successive generations.

SUMMARY OF THE INVENTION

The cultivar Jade Gloss has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jade Gloss'. These characteristics in combination distinguish 'Jade Gloss' as a new and distinct cultivar:

1. Full and densely foliated; uniformly mounded plant habit.

2. Upper leaf surfaces silvery gray in color with contrasting dark gray green venation; lower leaf surfaces dark red purple in color.
3. Numerous showy white and red purple-colored flowers arranged on erect panicles.
4. Excellent garden performance.

Plants of the new Heuchera can be compared to plants of the parent, the cultivar Silver Maps. In side-by-side comparisons conducted by the Inventor in Scottdale, Pa., plants of the new Heuchera differed from plants of the cultivar Silver Maps in the following characteristics:

1. Leaves of plants of the new Heuchera had more rounded lobes than leaves of plants of the cultivar Silver Maps.
2. Upper leaf surfaces of plants of the new Heuchera had less extensive leaf veining than upper leaf surfaces of plants of the cultivar Silver Scrolls.
3. Plants of the new Heuchera had shorter flowering stems than plants of the cultivar Silver Maps.

Plants of the new Heuchera can be compared to plants of the cultivar Silver Scrolls, disclosed in U.S. Plant Pat. No. 12,066. In side-by-side comparisons conducted by the Inventor in Scottdale, Pa., plants of the new Heuchera differed from plants of the cultivar Silver Scrolls in the following characteristics:

1. Leaves of plants of the new Heuchera were thicker and had deeper lobes than leaves of plants of the cultivar Silver Scrolls.
2. Upper leaf surfaces of plants of the new Heuchera had less extensive leaf veining than upper leaf surfaces of plants of the cultivar Silver Scrolls.
3. Plants of the new Heuchera had shorter flowering stems than plants of the cultivar Silver Scrolls.
4. Plants of the new Heuchera were more freely flowering than plants of the cultivar Silver Scrolls.

Plants of the new Heuchera can also be compared to plants of the cultivar Harmonic Convergence, disclosed in U.S. Plant Pat. No. 11,111. In side-by-side comparisons conducted by the Inventor in Scottdale, Pa., plants of the new Heuchera differed from plants of the cultivar Harmonic Convergence in the following characteristics:

1. Plants of the new Heuchera had smaller leaves than plants of the cultivar Harmonic Convergence.
2. Upper leaf surfaces of plants of the new Heuchera had less extensive leaf veining than upper leaf surfaces of plants of the cultivar Harmonic Convergence.
3. Plants of the new Heuchera had shorter flowering stems than plants of the cultivar Harmonic Convergence.
4. Lower surfaces of sepals of plants of the new Heuchera were white and red purple bi-colored whereas lower surfaces of sepals of plants of the cultivar Harmonic Convergence was red purple.

BRIEF DESCRIPTION OF THE PHOTOGRAPH

The accompanying colored photograph illustrates the overall appearance of the new Heuchera, showing the colors as true as it is reasonably possible to obtain in colored reproductions of this type. Colors in the photograph may differ slightly from the color values cited in the detailed botanical description which accurately describe the colors of the new Heuchera. The photograph comprises a side perspective view of a typical flowering plant of 'Jade Gloss' that was about one year old and grown in the landscape.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Scottdale, Pa. in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C. Measurements and numerical values represent averages taken from a group of flowering plants.

Botanical classification: *Heuchera sp.* cultivar Jade Gloss.

Parentage: Self-pollination of *Heuchera sp.* cultivar Silver Maps, not patented.

Propagation:

*Type*.—By cuttings.

*Time to initiate roots*.—Summer: About 15 days at 23° C. Winter: About 21 days at 17° C.

*Time to produce a rooted cutting*.—Summer: About 45 days at 23° C. Winter: About 60 days at 17° C.

*Root description*.—Fine, fibrous and well-branched.

Plant description:

*Appearance*.—Perennial; basal rosette plant habit with leaves developing from the base; densely foliated; full, mounded and uniform plant habit with upright panicles with showy white and red purple-colored flowers. Vigorous and robust growth habit.

*Plant size*.—Height: Soil level to top of foliar plane: About 14 cm. Soil level to top of panicles: About 50 cm. Diameter or spread: About 40 cm.

*Foliage description*.—Arrangement: Basal rosette, simple. Length: About 7.5 cm. Width: About 7 cm. Shape: Cordate; 7-lobed. Apex: Broadly obtuse, lobed. Base: Cordate. Margin: Crenate with fine ciliation; lobed. Texture: Upper surface: Rough; glabrous. Lower surface: Rough; slightly pubescent. Venation pattern: Palmate, reticulate. Color: Developing leaves, upper surface: 198A underlain with 187A. Developing leaves, lower surface: 187B. Fully expanded leaves, upper surface: 198A. Fully expanded leaves, lower surface: 187B. Venation: Upper surface: 189A underlain by 200A. Lower surface: 187B. Petiole: Length: About 12 cm. Diameter: About 2 mm. Texture, upper and lower surfaces: Smooth, glabrous. Color, upper and lower surfaces: 187B.

Flower description:

*Appearance/arrangement*.—Single campanulate flowers arranged on numerous erect panicles; about 150 to 200 flowers and flower bud per flowering stem. Flowers face outward to slightly upright. Flowering continuous with about 15 flowering stems per plant developing throughout the flowering period. Flowers persistent. Flowers not fragrant.

*Time of flowering*.—Under natural conditions, plants flower May to July in Scottdale, Pa.

*Inflorescence longevity*.—Individual inflorescences last about one week on the plant.

*Inflorescence size*.—Length: About 50 cm. Diameter: About 8 cm.

*Flower size*.—Diameter: About 4.5 mm. Depth (height): About 7 mm.

*Flower buds*.—Height: About 4.5 mm. Diameter: About 3 mm. Shape: Bulbous. Color, at stage of showing color: 57D.

*Sepals*.—Quantity/arrangement: Five sepals; radially symmetrical and fused at base. Length: About 6 mm. Width: About 2 mm. Shape: Elongate. Apex: Obtuse. Margin: Entire. Texture: Pubescent. Color: When opening and fully opened, upper surface: White, close to 155D. When opening and fully opened, lower surface: Margin, white, close to 155D; mid-section and base, 57D.

*Petals*.—Quantity/arrangement: Five minute petals; radially symmetrical and fused at base. Length: About 3.5 mm. Width: About 0.7 mm. Shape: Spatulate. Apex: Acute. Margin: Entire. Texture: Slightly pubescent. Color: When opening, upper and lower surfaces: Close to 155D. Fully opened, upper and lower surfaces: Close to 155D.

*Peduncle*.—Strength: Strong; flexible. Aspect: Erect. Length: About 50 cm. Diameter: About 2.2 mm. Texture: Smooth. Color: 187B.

*Pedicels*.—Strength: Strong; wiry. Aspect: About 30° from vertical. Length: About 3.5 cm. Diameter: About 0.2 mm. Texture: Pubescent. Color: 187B.

*Reproductive organs*.—Androecium: Stamen number: Five per flower. Anther shape: Oval. Anther length: About 0.2 mm. Anther color: 25A. Amount of pollen: Moderate. Pollen color: 23B. Gynoecium: Pistil number: Two per flower. Pistil length: About 6 mm. Stigma shape: Rounded. Stigma color: 157C. Style length: About 4 mm. Style color: 157C. Ovary color: 157D.

*Seed*.—Amount: Abundant. Length: About 0.6 mm. Diameter: About 0.3 mm. Color: Close to 202A.

Disease/pest resistance: Resistance to pathogens and pests common to Heuchera has not been observed on plants grown under commercial conditions.

Temperature tolerance: Plants of the new Heuchera have demonstrated good tolerance to night temperatures as low as −35° C. and day temperatures as high as 45° C.

It is claimed:

1. A new and distinct cultivar of Heuchera plant named 'Jade Gloss', as illustrated and described.

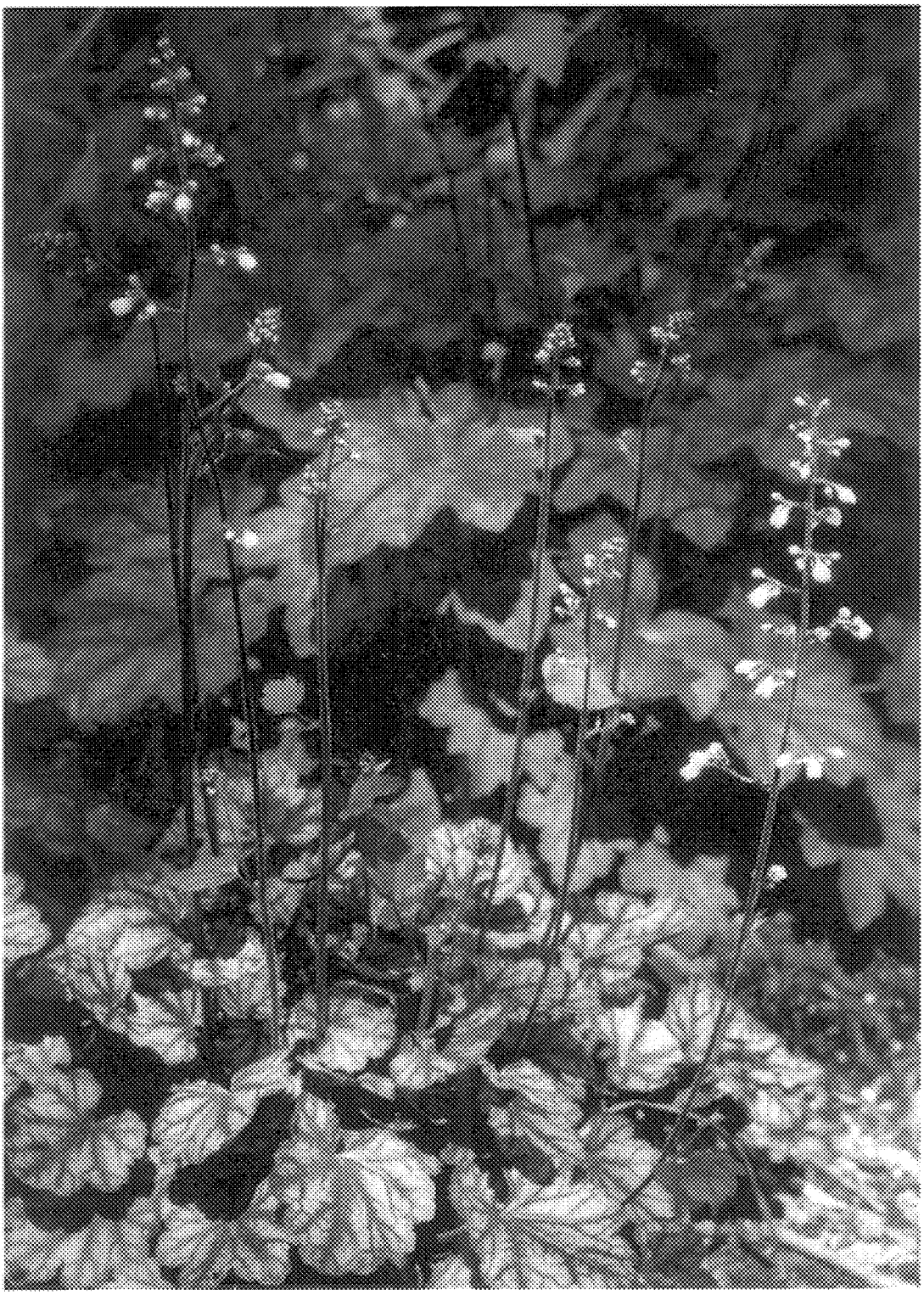

* * * * *